(12) United States Patent
Painchaud et al.

(10) Patent No.: US 6,415,172 B1
(45) Date of Patent: Jul. 2, 2002

(54) OPTICAL IMAGING OF TURBID MEDIA WITH DEPTH-RELATED DISCRIMINATION

(75) Inventors: Yves Painchaud, Sillery; Stéphane Chatigny, Quebec; Michel Morin, Cap-Rouge, all of (CA)

(73) Assignee: Art Advanced Research Technologies, Inc., St-Laurent (CA)

(*) Notice: Subject to any disclaimer, the term of this patent is extended or adjusted under 35 U.S.C. 154(b) by 0 days.

(21) Appl. No.: 09/489,528

(22) Filed: Jan. 21, 2000

(30) Foreign Application Priority Data

Jan. 22, 1999 (CA) .............................................. 2259900

(51) Int. Cl.[7] ............................................... A61B 5/00
(52) U.S. Cl. ........................ 600/407; 600/476; 356/432
(58) Field of Search ................................. 600/407, 425, 600/473, 476; 356/337, 338, 432; 250/341.1, 358.1

(56) References Cited

U.S. PATENT DOCUMENTS

| | | |
|---|---|---|
| 5,447,159 A | 9/1995 | Schultz |
| 5,666,434 A | 9/1997 | Nichikawa et al. |
| 5,699,798 A | 12/1997 | Hochman et al. |
| 5,796,862 A | 8/1998 | Pawlicki et al. |
| 5,799,656 A | 9/1998 | Alfano et al. |
| 5,808,304 A | 9/1998 | Parent et al. |
| 5,820,558 A | 10/1998 | Chance |
| 5,876,339 A | 3/1999 | Lemire |
| 5,899,865 A | 5/1999 | Chance |
| 5,907,406 A | 5/1999 | Papaioannou et al. |
| 5,999,639 A | 12/1999 | Rogers et al. |
| 5,999,836 A | 12/1999 | Nelson et al. |

FOREIGN PATENT DOCUMENTS

| | | |
|---|---|---|
| DE | 41 30 369 A1 | 12/1991 |
| EP | 0 108 617 A1 | 3/1983 |

OTHER PUBLICATIONS

G. Jarry, et al. "Laser tomography of heterogeneous scattering media using spacial and temporal resolution", *Medial physics and imaging*, Medical & Biological Engineering & Computing, Mar. 1993, pp. 157–164.

*Primary Examiner*—Ruth S. Smith
(74) *Attorney, Agent, or Firm*—Fay, Sharpe, Fagan, Minnich & McKee, LLP

(57) ABSTRACT

The method for scanning a turbid medium involves displacing an optical signal source over a first face of the medium and a corresponding optical detector over an opposite face from one respective spatial location to another. Each spatial location is associated with a corresponding input region on the first face and a corresponding output region on the opposite second face. The optical detector in response to optical signals detected from each of the output regions generates a primary set of image data, secondary and/or tertiary image data by scanning the turbid medium using input regions and output regions of different sizes. The various sets of image data obtained may be manipulated in any manner, namely subjected to a data processing technique, so as to, for example, highlight the differences or similarities between the images.

9 Claims, 4 Drawing Sheets

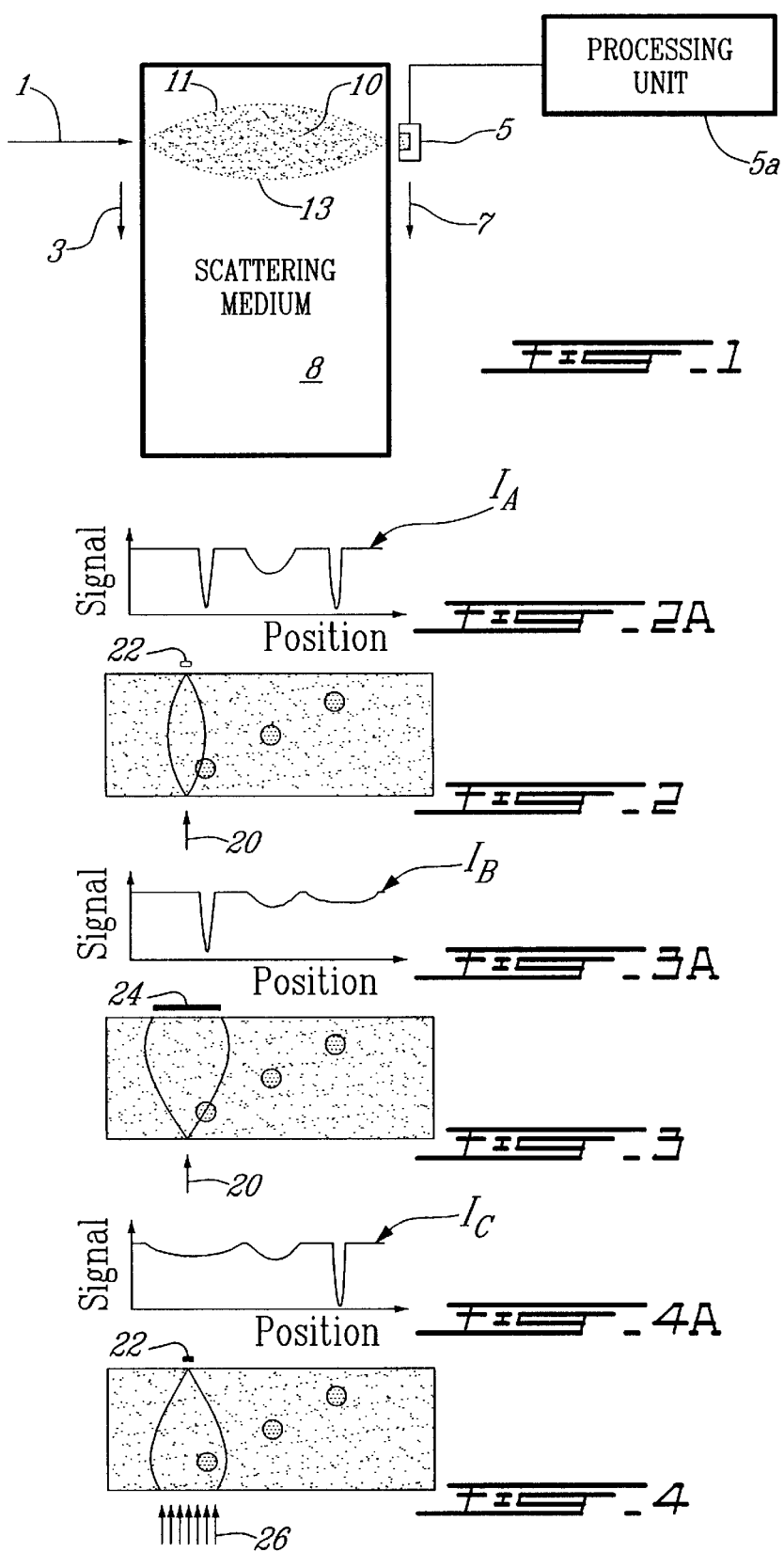

OPTICAL IMAGING OF TURBID MEDIA WITH DEPTH-RELATED DISCRIMINATION

FIELD OF THE INVENTION

The present invention relates to optical imaging of turbid media, e.g. breast tissue.

BACKGROUND OF THE INVENTION

Optical mammography is likely to become a relevant technology for breast cancer detection. Light scatting is the main problem that limits the potential of efficiently detecting small lesions especially when located in the central region of the breast. Structures close to surface are easily detected by optical techniques while more deep structures are more difficultly detected. A technique to preferentially probe in the central region of the breast is thus of interest.

The present text will refer by way of example only to breast tissue; however, other types of turbid media (i.e. other types of (living) tissue) may also be imaged using the techniques described herein.

Optical imaging of turbid media has been the subject of much research activity and has seen an increase in interest since the early 1990's. This type of imaging is based on the fact that the propagation of light in a turbid medium depends on the absorption and scattering properties of the medium. Absorption results from energy level transitions of the constituent atoms and molecules in the medium. The absorption property of the medium is quantified by its absorption coefficient $\mu_a$ defined as the probability of a photon being absorbed per infinitesimal pathlength. Scattering results from variations in the index of refraction of the different structures present in the medium. In a highly diffusive medium, scattering is quantified by the reduced scattering coefficient $\mu'_s$, defined as the probability of a photon being isotropically scattered per infinitesimal pathlength. Characteristics such as intensity, coherence and polarization of the incident light change as it is absorbed and scattered by the medium resulting in diffuse transmittance of the light. In particular, scattering causes a collimated laser beam to spread over a sizeable volume element. This complicates the imaging of a turbid medium. Special imaging modalities must be implemented to offset the detrimental light diffusion. For example, time-resolved methods use short light pulses from a fast laser source to illuminate the medium. The emergent light is collected by a fast detector capable of reproducing its time variation, which can provide further information about the turbid medium. A simple data processing approach in this case is time-gating, by which only the earliest part of the output light pulses is used to produce an image. This amounts to using only the light with the straightest trajectory through the scattering medium, thus improving spatial resolution (please see J. C. Hebden and R. A. Kruger, "Transillumination imaging performance: Spatial resolution simulation studies". Med. Phys. 17, 41–47 (1990)) Reference may also be made to the following documents for additional information with respect to optical scanning techniques: S. B. Colak, D. G. Papaioannou, G. W. Hooft, M. B. Van der Mark, H. Schomberg, J. C. J. Paasschens, J. B. M. Melissen, and N. A. A. J. Van Asten, "Tomographic image reconstruction from optical projections in light-diffusing media", Appl. Opt. 36, 180–213 (1997); M. S. Patterson, B. Chance, and B. C. Wilson, "Time-resolved reflectance and transmittance for the non-invasive measurement of tissue optical properties", Appl. Opt. 28, 2331–2336 (1989); D. Contini, F. Martelli, and G. Zaccanti, "Photon migration through a turbid slab described by a model based on diffusion approximation. I. Theory", Appl. Opt. 36, 4587–4599 (1997); M. Morin, S. Chatigny, A. Mailloux, Y. Painchaud, and P. Beaudry. "Time-domain perturbation analysis of a scattering slab", in *Optical Tomography and Spectroscopy of Tissue III*, B. Chance, R. R. Alfano, and B. J. Tromberg, eds., Proc. SPIE 3597, 67–78 (1999); Y. Painchaud, A. Mailloux, M. Morin, S. Verreault and P. Beaudry, "Time-domain optical imaging: discrimination between scattering and absorption", Appl. Opt. 38, 3686–3693 (1999); as well as U.S. Pat. No. 5,808,304).

The strong interest in optical imaging of scattering media stems from the need for biomedical diagnostic techniques that are safe and non-invasive. The optical properties of biological tissues are at the heart of optically based biomedical diagnostic techniques. As for the general case of a turbid medium, the manner in which light propagates through tissue depends on its absorption and scattering properties. Thus, if abnormal tissue can be said to differ from normal in its absorption or scattering of light for some physiological or morphological reason, it then becomes possible to optically differentiate between normal and abnormal conditions. A specific application is optical mammography where tumors could be differentiated from normal breast tissue on the basis of optical properties.

SUMMARY OF THE INVENTION

It would, for example, be advantageous to have a mechanism for the detection of an anomaly(ies) in turbid medium such as for example a tumour in tissue such as breast tissue.

Accordingly, the present invention in one aspect provides in a method for scanning a turbid medium for generating an image thereof for the detection of one or more anomalies contained within the turbid medium, said turbid medium having a first face and an opposite second face, wherein said turbid medium is scanned by displacing an optical signal source and a corresponding optical detector from one respective spatial location to another about the turbid medium, each spatial location being associated with a corresponding input region on said first face and a corresponding output region on the opposite dsecond face, said optical signal source directing an optical signal (e.g. laser beam) to each of said input regions, said optical detector in response to optical signals detected from each of said output regions sending corresponding detector output signal data to an image processing means for generating a set of image data of the turbid medium, the improvement comprising generating a primary set of image data derived by scanning said turbid medium using for each input region a first input region of predetermined size and using for each output region a first output region of predetermined size, and generating a secondary set of image data derived by scanning said turbid medium using for each input region said first region of predetermined size and using for each output region a second output region of predetermined size.

The present invention in another aspect provides in a method for scanning a turbid medium for generating an image thereof for the detection of one or more anomalies contained within the turbid medium, said turbid medium having a first face and an opposite second face, wherein said turbid medium is scanned by displacing an optical signal source and a corresponding optical detector from one respective spatial location to another about the turbid medium, each spatial location being associated with a corresponding input region on said first face and a corresponding output region on the opposite second face, said optical signal source directing an optical signal (e.g. laser beam) to each of said input regions, said optical detector in response to optical signals detected from each of said output regions sending corresponding detector output signal data to an image processing means for generating a set of image data of the turbid medium, the improvement comprising generating a primary set of image data derived by scanning said turbid medium using for each input region a first input region of predetermined size and using for each output region a first output region of predetermined size, and generating a further set of image data derived by scanning said turbid medium using for each input region a second input region of predetermined size greater than that of said first input region and using for each output region said first output region of predetermined size.

The present invention in another aspect provides in a method for scanning a turbid medium for generating an image thereof for the detection of one or more anomalies contained within the turbid medium, said turbid medium having a first face and an opposite second face, wherein said turbid medium is scanned by displacing an optical signal source and a corresponding optical detector from one respective spatial location to another about the turbid medium, each spatial location being associated with a corresponding input region on said first face and a corresponding output region on the opposite second face, said optical signal source directing an optical signal (e.g. laser beam) to each of said input regions, said optical detector in response to optical signals detected from each of said output regions sending corresponding detector output signal data to an image processing means for generating a set of image data of the turbid medium, the improvement comprising generating a primary set of image data $I_A$ derived by scanning said turbid medium using for each input region a first input region of predetermined size and using for each output region a first output region of predetermined size, generating a secondary set of image data $I_B$ derived by scanning said turbid medium using for each input region said first input region of predetermined size and using for each output region a second output region of predetermined size greater than that of said first output region and generating a tertiary set of image data $I_C$ derived by scanning said turbid medium using for each input region a second input region of predetermined size greater than that of said first input region and using for each output region said first output region of predetermined size.

In accordance with the present invention the various sets of image data may be generated in any desired or necessary order.

In accordance with the present invention, the various sets of image data obtained as described herein may be manipulated in any manner (i.e. subjected to a data processing technique) so as to for example highlight the differences and/or similarities between the images (e.g., to obtain a composite set of image data indicative of an anomaly(ies) (e.g. breast tumour) in the body of the turbid medium); such manipulation or data processing treatment may be carried out by simple subtraction or by exploiting more sophisticated techniques such as for example K–L transforms. Thus, for example, the method(s) described herein may comprise (a) combining said primary set of image data and said secondary set of image data so as to generate a product set of image data wherein the similarities and/or differences between the said primary set of image data and said secondary set of image data are highlighted.; (b) combining said primary set of image data and said further set of image data so as to generate a product set of image data wherein the similarities and/or differences between the said primary set of image data and said further set of image data are highlighted.; (c) combining said primary set of image data said secondary set of image data and said tertiary set of image data so as to generate a product set of image data wherein the similarities and/or differences between said primary set of image data, said secondary set of image data and said tertiary set of image data are highlighted; etc. Thus, more particularly, for example, a composite set of image data may be generated by subtracting the secondary set of image data from the primary set of image data: a composite set of image data may be generated by subtracting the further set of image data from the primary set of image data; a composite set of image data may be generated in accordance with equation $I_B + I_C - I_A$.

Preferably, the method involves combining the primary set of image data and the secondary set of image data so as to generate a product set of image data wherein similarities and/or differences between the primary set of image data and the secondary set of image data are highlighted.

In accordance with the present invention a system for performing optical imaging measurements on a turbid medium in accordance with the method(s) as described herein may, for example, comprise any suitable (known) means for generating a collimated optical signal (e.g. laser)

directing means for directing said optical signal to an input area or region of predetermined size on a face on one side of the turbid medium (e.g. using a suitable optical fiber)

detection means for detecting a optical output signal from a second area or region of predetermined size on the face of the turbid medium on the opposite side of said turbid medium (e.g. photomuliplier tube, streak camera, etc.); the detection means may include optical fibers for directing the optical signal to the component of the detection means which may convert the optical signal to an output (e.g. analogue or digital electrical) signal; and means (e.g. computer) for processing said optical output signals (in any known manner) so as to obtain a set of image data (e.g. data which may be projected onto the screen of a computer monitor, be printed on a printer, be further processed, stored in computer memory, etc. . . ).

The system may also of course incorporate any suitable mechanism or means for manipulating the size of the input and output regions as referred to herein.

It is to be understood herein (i.e. for the purposes of the present invention) that the optical signal(s) may be of electromagnetic radiation which is not only in the visible but as well as in the infra-red or the near infra-red part of the spectrum keeping in mind the purpose of the signal; the initial optical signal may for example be a laser beam.

The technique of the present invention may as mentioned above involve two or three (successive) scans of the turbid medium (e.g. breast tissue) so as to provide two or three projection images. These two or three images may be used to image structures according to their depth inside the breast. The first image shows all the structures as in the usual optical techniques. A second image preferentially highlights the structures near the input surface. Another, third image preferentially highlights the structures near the output surface. By a combination of two or three of the images, it is possible to highlight the structures in the central region of the breast and attenuate the structures near the surfaces.

BRIEF DESCRIPTION OF THE DRAWINGS

In the figures which illustrate example embodiments of the present invention:

FIG. 1 illustrates in schematic fashion a Scanning system for imaging through a turbid medium.

FIG. 2 illustrates in schematic fashion a Scanning system for imaging through a turbid medium having a point-source/point-detector configuration FIG. 2A shows a graph for the configuration of FIG. 2 wherein the qualitatively indicates the transmitted light versus transverse position for each configuration FIG. 3 illustrates in schematic fashion a Scanning system for imaging through a turbid medium having a point-source/large-area detector configuration FIG. 3A shows a graph for the configuration of FIG. 3 wherein the qualitatively indicates the transmitted light versus transverse position for each configuration FIG. 4 illustrates in schematic fashion a Scanning system for imaging through a turbid medium having a large-area source/point-detector configuration FIG. 4A shows a graph for the configuration of FIG. 4 wherein the qualitatively indicates the transmitted light versus transverse position for each configuration;

DETAILED DESCRIPTION OF THE PREFERRED EMBODIMENT

Figures 5, 6:
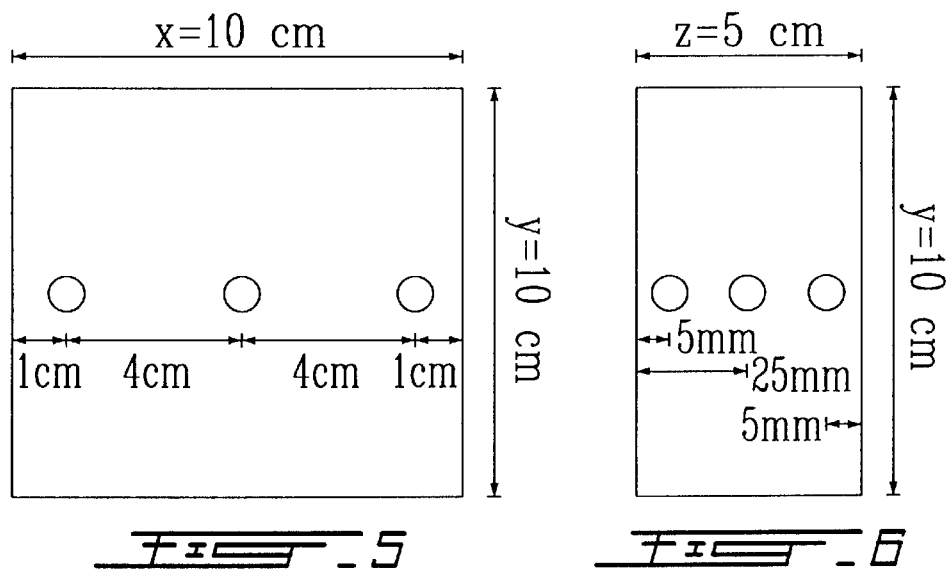
FIG. 5 illustrates a front view of a phantom.
FIG. 6 illustrates a side view of the phantom of FIG. 5.

In biomedical optical imaging, two types of images can be generated: 3D reconstructed images and 2D projection images. The former are produced using tomography which is typically based on a multi-point geometry involving a large number of detectors (see S. B. Colak, D. G. Papaioannou, G. W. Hooft, M. B. Van der Mark, H. Schomberg, J. C. J. Paasschens, J. B. M. Melissen, and N. A. A. J. Van Asten, "Tomographic image reconstruction from optical projections in light-diffusing media", Appl. Opt. 36, 180–215 (1997)). Its advantage is that 3D images are generated, however, measurements and reconstructions are potentially time-consuming. 2D projection images are based on the detection of the light that enters the medium through a small area, that propagates through the medium and that exits the medium over a small detection area facing the entrance area. The image is generated by measuring the transmitted light in such a manner at a large number of points as both the light beam incident on the medium and the detection device are scanned synchronously along the surface of the medium. This imaging scheme is illustrated in FIG. 1 wherein an arrow 1 is indicative of a laser beam; wherein arrow 3 is indicative of the scanning direction of the beam 1; wherein the optical detector means is indicated by reference numeral 5; wherein arrow 7 is indicative of the scanning direction of the optical detector means 5; and wherein the scattering medium is designated by the reference numeral 8. For the scanning system schematically illustrated in FIG. 1 (known) means are provided (not shown) whereby the laser beam 1 and the optical detector means 5 are respectively displaced in the direction of the arrows 3 and 7 in synchronise fashion, i.e. such that the optical detector 5 is always opposite the laser beam 1. Although also not shown (in detail) in FIG. 1, the optical detector 5 (as well as the means for generating the laser beam and the means for directing the laser beam to the scan surface of face) may be coupled in any (known) manner to a suitable (known) processing unit (e.g. computerised processing system) for ultimately generating or deriving an image (i.e. a set of image data) from the set of signal data obtained from the optical detector 5 during the scanning process. FIG. 1 does show in block diagram fashion a processing unit 5a coupled to the optical detector 5 for processing the detector output signal data into image data.

The scanning technique illustrated by the system in FIG. 1 has the advantage that it is fast and compatible with time-resolved measurements. However, information is limited to two dimensions, the detected light giving information about a volume extending over the whole line-of-sight joining the input point of the laser beam and the detector. This is illustrated in FIG. 1, where the gray region 10 within the dotted lines 11 and 13 represents the volume through which detected photons have most likely propagated. The shape of this volume can be understood by considering that all photons enter the scattering medium at the same point and all detected photons leave it through a small area facing the detector. On the other hand, scattering allows detected photons to wander away from the direct line-of-sight joining the laser beam and the detector, this wandering being maximum at the half-distance between the two. As illustrated in FIG. 1, the scanning technique provides no longitudinal information, since the probed volume extends over the whole thickness of the scattering medium. Moreover, a small volume heterogeneity, with optical properties different from those of the scattering medium, is more likely to be visible when located close to the input point of the laser beam or the output point facing the detector. This is so because it is then probed by most detected photons, whereas a smaller fraction of detected photons propagate through the same heterogeneity standing in the middle of the scattering medium, where the probed volume is the widest. For optical mammography this can be troublesome, as a tumor located deep within breast tissue could be overshadowed by strongly absorbing structures such as veins located near the surface.

The detection method in accordance with the present invention may provide for the basic evaluation of heterogeneity depth in a scattering medium (e.g. turbid medium) to be used in conjunction with optical imaging based on light transmittance measurement and the production of projection images. Depth assessment is necessary for a full 3-D localization of the heterogeneity. It can also aid visualization of structures located in the central plane of a turbid medium by identifying those structures located close to surfaces, which can then be taken out of images. Finally, knowledge of the longitudinal position of the heterogeneity can be used during data processing to improve the qualification of the optical contrast of the said heterogeneity with regards to the surrounding scattering medium. Within the context of mammography, this can help in tissue recognition.

The present invention which may be referred to by way of example as Dual Spatial Integration (DSI) permits localization by separating the scattering medium into two or three longitudinal zones: a zone close to the input surface where the light is injected, a central zone and/or a zone close to the output surface where the light is detected. By dividing the medium into two or three segments, structures close to surfaces can be extracted and set aside, and structures located in the bulk enhanced.

FIGS. 2, 3 and 4 (as well as respective FIGS. 2A, 3A and 4A) illustrate (in schematic fashion) how detection surfaces and input beams of different sizes may be used to achieve a certain degree of longitudinal localization of an inclusion within a scattering slab, e.g. by appropriately modifying the input or output region sizes while maintaining the other variables (i.e. essentially the same) during the generation of each of the sets of image data during the scanning procedures.

DSI may as mentioned above use three different source-detector configurations to achieve this sectioning; example configurations are illustrated schematically in FIGS. 2, 3 and 4; for each of the shown configurations the same scattering medium is used, i.e. a scattering medium containing three inclusions at different depths (i.e. the three black dots or circles shown in these figures).

Specifically, the first configuration (i.e. configuration 1) shown in FIG. 2 comprises a point source (i.e. small area input laser beam) 20 and a point detector (i.e. small area detector) 22 which are used as the base configuration. The second configuration (i.e. configuration 2) shown in FIG. 3 comprises a point source (i.e. small area input laser beam) 20 and a large detector (i.e. large area detector) 24. The third configuration (i.e. configuration 3) shown in FIG. 4 comprises a large source (i.e. large area input laser beam) 26 and a point detector (i.e. small area detector) 22 are used as the base configuration. For each of the configurations the laser beam is generated in any known suitable fashion; the light leaving the scattering medium is detected by any known suitable detector; the beam and detector (or alternatively, the medium itself) are (is) displaced (i.e. so as to facilitate scanning of the medium) longitudinally in synchronise fashion in any (known) suitable fashion across opposed faces of the scattering medium; and images are generated from the detector signals by any suitable known processing system (e.g. computer system). For each of FIGS. 2, 3 and 4: the gray-shaded rectangle is the turbid medium; the dark circles indicate the placement of the inclusions or heterogeneities in the turbid medium; the dark line above each rectangle refers to either a large area detector (long line) or a point detector (short line)—reference numbers 22 and 24; the arrows indicate the type of source used: single arrow for a point source and multiple arrows for a large area source, namely the elements specified by reference numbers 20 and 26; and the thin lines within the turbid medium delimitate qualitatively the volume being probed by detected photons. The FIGS. 2A, 3A and 4A show graphs wherein each respectively qualitatively indicates the transmitted light versus transverse position for each configuration.

In accordance with the present invention the detection method may proceed as discussed hereinafter. The scattering medium is scanned with the scanning configuration shown in FIG. 2 and an image ($I_A$) generated. In the image ($I_A$) so obtained, structures close to both the exit and entrance faces are highlighted relative to those within the bulk. As the laser beam and detector are moved transversely along the surface of the scattering medium, the inclusions close to the input and output surfaces have a stronger impact on the detected light, as discussed above. This is represented qualitatively by the graph shown in FIG. 2A, which depicts the detected light (signal) as a function of the position across the surface of the scattering medium. A large area detector is then substituted for the point detector so as to obtain the second configuration shown in FIG. 3. This changes the volume that is probed by detected photons, as illustrated in FIG. 3. The scattering medium is scanned with this second configuration and an image ($I_B$) generated. In this image ($I_B$), structures closest to the entrance face are highlighted, relative to those within the bulk or close to the exit face, because they are probed by a larger fraction of the detected photons. This is represented qualitatively by the graph shown in FIG. 3A, which depicts the detected light (signal) as a function of the position across the surface of the scattering medium. Thirdly, a large area source is substituted for the point source and a point detector replaces the large area detector so as to obtain the third configuration. This changes again the shape of the volume being probed by detected photons, as shown in FIG. 4. The scattering medium is scanned with this third configuration and an image ($I_C$) generated. In this image ($I_C$), structures closest to the exit face are now highlighted relative to those within the bulk or close to the entrance face. This is represented qualitatively by the graph shown in FIG. 4A, which depicts the detected light (signal) as a function of the position across the surface of the scattering medium.

If images $I_B$ and $I_C$ (i.e. their image or signal data) are added and image $I_A$ (i.e. its image or signal data) subtracted, structures located within the bulk of the scattering medium can be more readily visualized than in images generated with the base configuration ($I_A$) alone.

It is to be understood herein that the expression "small area" refers to a surface whose diameter is relatively small compared to the scattering (turbid) medium thickness, while the expression "large area" is to be understood as referring to a surface whose diameter is on the same order of magnitude as the scattering (turbid) medium thickness.

Application of DSI to the geometry illustrated in FIGS. 5 and 6 was evaluated numerically and experimentally. As shown in FIG. 6 the scattering medium is a 5 cm-thick slab containing three identical inclusions located at 5, 25 and 45 mm from the entrance face of the slab. The inclusions are at a distance of 4 cm from one another in a direction parallel to the face of the slab. The slab is 10 cm long (FIG. 5) with the inclusions spaced 4 cm apart from the nearest neighbour inclusion.

Figure 7:
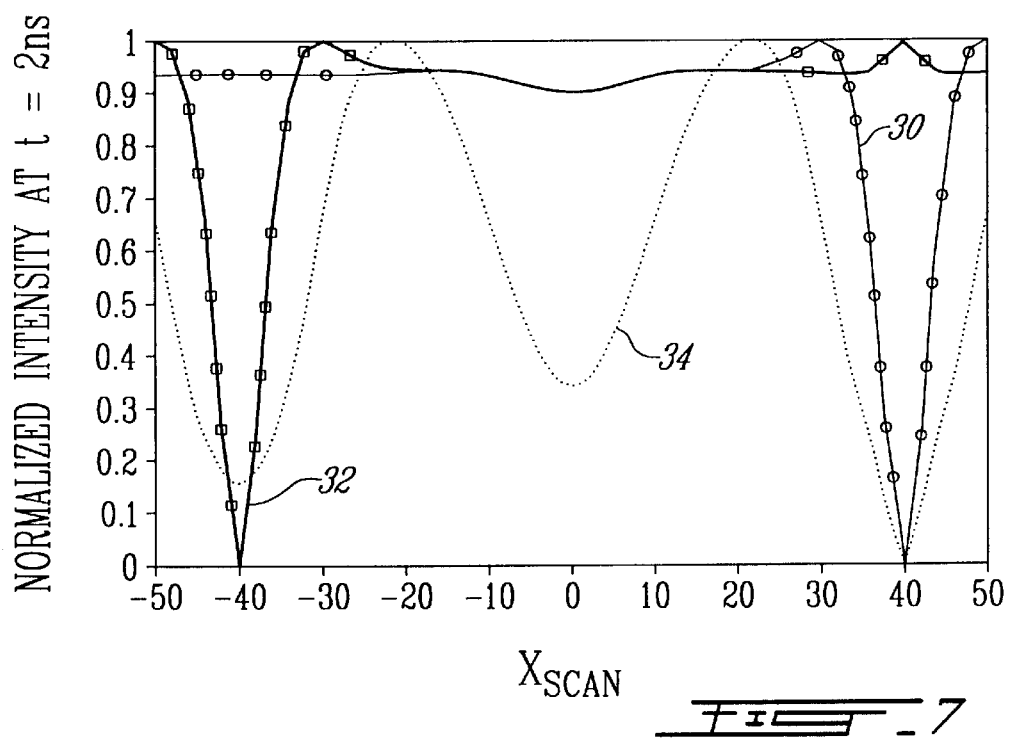
FIG. 7 is a graphic illustration of Spatial profile combination used to enhance longitudinal discrimination.

For the numerical simulations, the turbid medium was assumed to be purely scattering ($\mu_S$=1 mm$^{-1}$, $\mu_S$=0 mm$^{-1}$). The inclusions were assumed to be point-like, i.e. to have a vanishingly small volume. They were also assumed to differ from the scattering medium only in their absorption coefficient, such that (volume)$_{inclusion}$ multiplied by ($\mu_a$)$_{inclusion}$=5 mm$^2$. The surface areas of both the large-area detector and source were set at 400 mm$^2$. The diffusion model (see M. S. Patterson, B. Chance, and B. C. Wilson, "Time-resolved reflectance and transmittance for the non-invasive measurement of tissue optical properties", Appl. Opt. 28, 2331–2336 (1989)), adapted to account for the refractive index mismatch between the turbid medium and the surrounding environment (see D. Contini, F. Martelli, and G. Zaccanti, "Photon migration through a turbid slab described by a model based on diffusion approximation. I. Theory", Appl. Opt. 36, 4587–4599 (1997)), was used to describe light propagation through the simulated medium. The effect of the placement of an inclusion into the medium was modelled using a perturbation analysis (see M. Morin, S. Chatigny, A. Mailloux, Y. Painchaud, and P. Beaudry. "Time-domain perturbation analysis of a scattering slab", in *Optical Tomography and Spectroscopy of Tissue III*, B. Chance, R. R. Alfano, and B. J. Tromberg, eds., Proc. SPIE 3597, 67–78 (1999)). The calculations assumed that infinitely short pulses of light were launched into the scattering medium. The transmitted light intensity calculation was limited to photons exiting the medium 2 ns after they entered the slab. The spatial intensity profiles $P_A$, $P_B$ and $P_C$ thus obtained with each detection configuration were calculated for a transverse scan along a line joining the inclusions; $P_A$ is profile for configuration 1, $P_B$ is profile for configuration 2 and $P_C$ is profile for configuration 3. These profiles were then normalized and combined to enhance depth discrimination, as discussed above. The results of these combinations are shown in FIG. 7 after their normalization to unity. FIG. 7 is a graphic illustration of Spatial profile combinations used to enhance longitudinal discrimination. The origin of the abscissa refers to the position of the middle inclusion (see FIG. 5: Front View). The value of $x_{scan}$ refers to the displacement with respect to this origin along the front surface of the medium (see FIG. 3: Front View). $P_A$ refers to the spatial profiles calculated with scanning system configurations shown in FIG. 2, 3 and 4 (i.e. namely, configuration 1, 2 and 3). In FIG. 7 for the profile of $P_A$ minus $P_B$ is illustrated by the graph line which contains the symbols - - - β- - (designated by the reference number 30); the profile of $P_A$ minus $P_C$ is illustrated by the graph line which contains the symbols - - - □- - (designated by the reference number 32); the profile of $P_B$ plus $P_C$ minus $P_A$ is illustrated by the graph line which does not contain any symbol (designated by the reference number 34).

Referring to FIG. 7, as expected, when the profile for configuration 3 ($P_C$) is subtracted from that of configuration 1 ($P_A$), only the signal from the inclusion near the input surface remains. On the other hand, subtracting the profile for configuration 2 ($P_B$) from that of configuration 1 ($P_A$) nearly eliminates the signal change caused by the inclusion close to the input surface. FIG. 7 also shows the effect when the profiles for configuration 2 ($P_B$) and 3 ($P_C$) are added together to get a resultant sum and the profile for configuration 1 ($P_A$) is subtracted from the resultant sum. These results clearly show how DSI permits to determine whether an inclusion is located close to either surface of the scattering medium.

The geometry in FIG. 5 was investigated experimentally using a phantom consisting of three inclusions placed into a 50 mm-thick cell containing a scattering solution of polystyrene microspheres. The inclusions were purely absorbing, 5 mm cylinders of black Delrin and positioned according to the geometry illustrated in FIG. 5. The scattering solution was non-absorbing with $\mu=1$ mm$^{-1}$. The laser light was carried close to the scattering medium using an input optical fiber. Similarly, the light transmitted through the medium was collected with an output optical fiber that carried the light to the detector. Using the divergence of light emerging from a fiber, a large area source was simulated by simply moving the input fiber far from the medium. Similarly, a large area detector was simulated by moving the output fiber far from the medium. Moving the input fiber away from the phantom such that photons were injected over a surface of 3.1 cm$^2$ functioned as the large area source. The large area detector was likewise achieved by moving the output fiber away from the phantom such that photons were collected over a surface of 3.8 cm$^2$.

Figure 8:
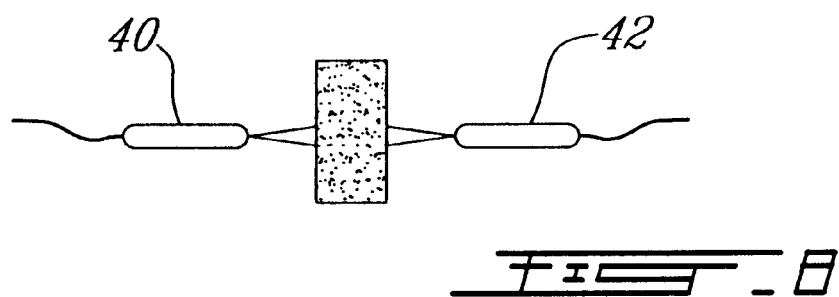
FIG. 8 schematically illustrates an optical fiber arrangement for a point-source/point detector configuration FIG. 9 schematically illustrates an optical fiber arrangement for a point-source/large-area detector configuration FIG. 10 schematically illustrates an optical fiber arrangement for a large-area source/point-detector configuration
Figure 9:
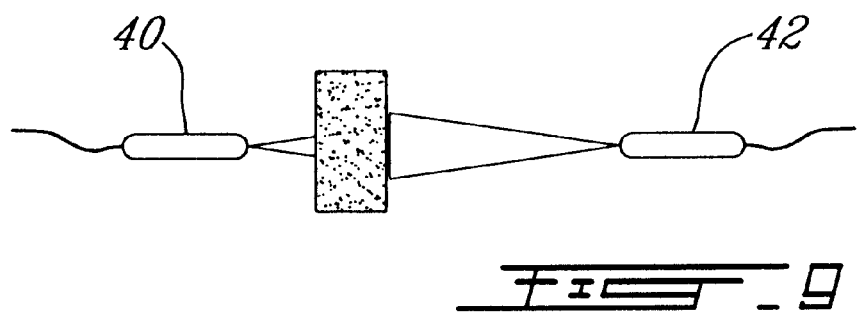
Figure 10:
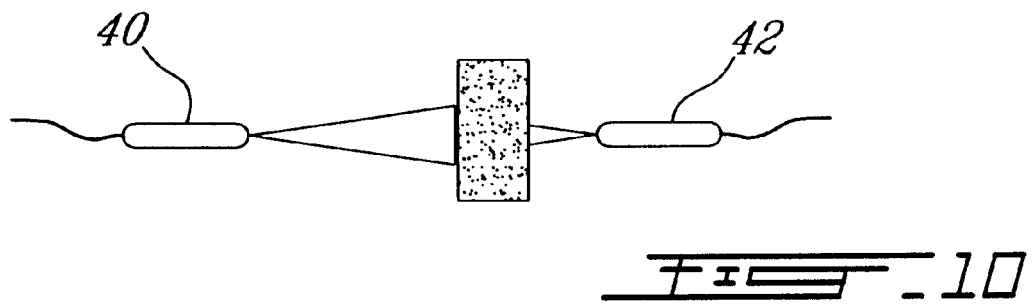

The three example optical fiber arrangements are illustrated in FIGS. 8, 9 and 10. FIG. 8 schematically illustrates an optical fiber arrangement for a point-source/point detector configuration, i.e. the optical fibers are configured and spaced so as to provide a scanning region or surface area and a detection region or surface area which have a small size and are more or less the same size. FIG. 9 schematically illustrates an optical fiber arrangement for a point-source/ large-area detector configuration i.e. the optical fibers 40 and 42 are configured and spaced so as to provide a scanning region or surface area and a detection region or surface area which are not the same size i.e. the detection area is larger than in FIG. 8—only the output fibers 42 are moved away from the phantom. FIG. 10 schematically illustrates an optical fiber arrangement for a large-area source/point-detector configuration i.e. the optical fibers are configured and spaced so as to provide a scanning region or surface area and a detection region or surface area which are not the same size i.e. the source area is larger than in FIG. 8—only the output fibers 40 are moved away from the phantom. Although the figures show that the size of the input and output areas or regions may be varied by displacing the fibres 40 and 42 an other type of mechanism may of course be used to effect the change in area. The phantom was scanned using each of these configurations using a near-infrared imaging system as described by Y. Painchaud, A. Mailloux, M. Morin, S. Verreault and P. Beaudry. "Time-domain optical imaging: discrimination between scattering and absorption", Appl. Opt. 38, 3686–3693 (1999)). The scan was cone by moving synchronously both the input and output fibers 40 and 42 respectively along the surface of the medium in two dimensions in order to sequentially illuminate the entire surface. The detected signal was digitized and sent to a computer that was used to construct the images based on the series of measurements performed during a scan, each measurement corresponding to one pixel of the image.

Figures 11, 12, 13, 14:
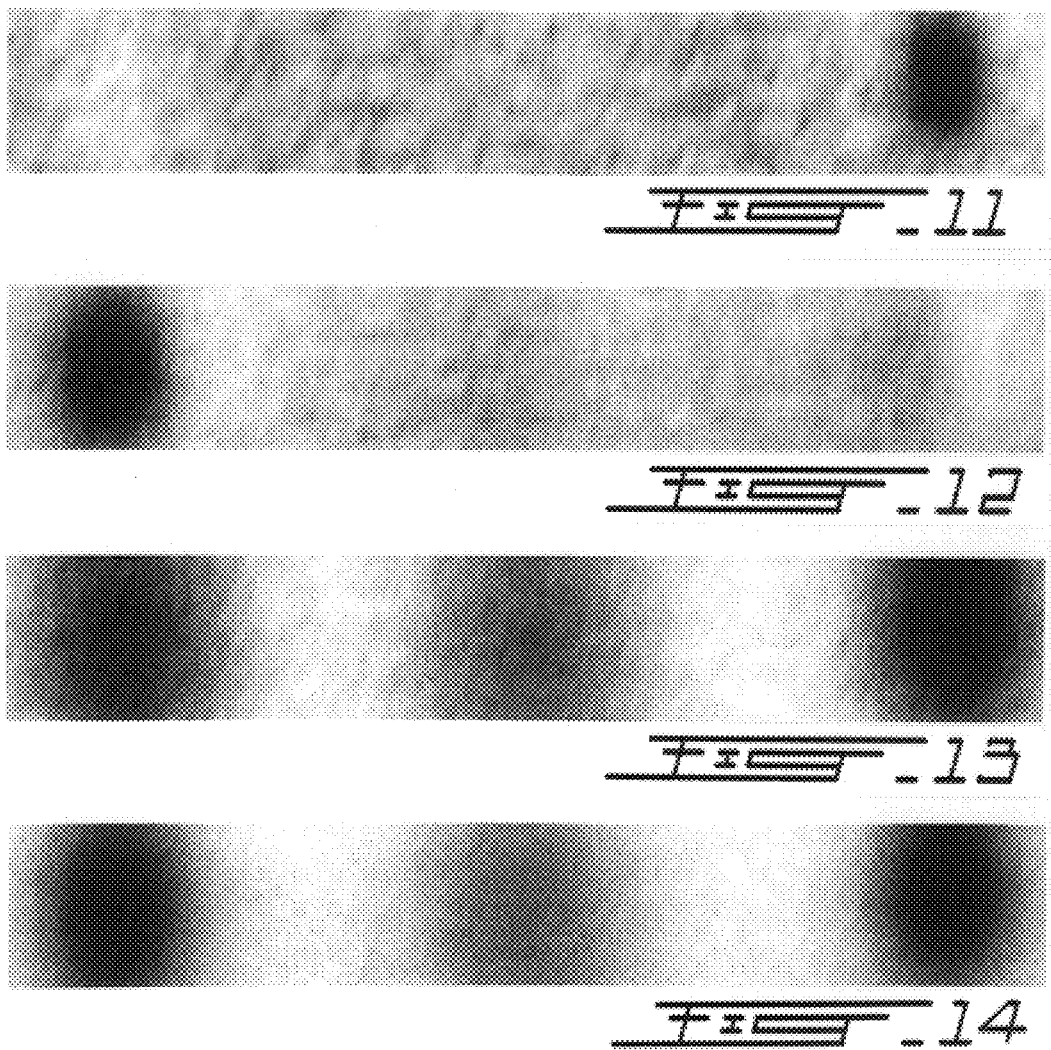
FIG. 11 is an illustration of the spatial profile combination for $P_A$–$P_B$ of a liquid phantom
FIG. 12 is an illustration of the spatial profile combination for $P_A$–$P_C$ of a liquid phantom
FIG. 13 is an illustration of the spatial profile combination for $P_B$+$P_C$–$P_A$ of a liquid phantom
FIG. 14 is an illustration of the spatial profile for $P_A$ of a liquid phantom

FIGS. 11, 12, 13 and 14 show the resultant projection images from scans of a liquid phantom. The horizontal axis corresponds to the transversal placement of the inclusions. These images were normalized and combined as described earlier for the simulations. The point detector/point source configuration resulted in the image in FIG. 14. FIGS. 11 and 12 show images demonstrating the success of the DSI method in extracting inclusions located near the surfaces. A comparison of the images in FIGS. 13 and 14 shows that the inclusion placed in the central plane of the phantom was highlighted relative to those near the surface using DSI.

As may be appreciated from the above, the Dual Spatial Integration technique (DSI) of the present invention is proposed as a tool to aid in the visualization of structures located in the central plane of a turbid medium. DSI represents an improvement with respect to the prior art in that one gains depth information content usually obtained with multi-point detection geometry without its concomitant time costs. This is achieved by using different source-detector configurations to section the medium, namely as follows:

1. The scattering medium is scanned using a point source and point detector (i.e. configuration 1).
2. An image ($I_A$) is generated based on the detected light using configuration 1. As an example, the detection of light can be done in a time-resolved manner in which only the first arrival photons are considered. The image can also be generated using indirect characteristics of the detected light as in the FIDM method described elsewhere.

3. The scattering medium is scanned using a point source and a large area detector (configuration 2).
4. A second image ($I_B$) is generated using the same method as in 2 but with configuration 2.
5. The scattering medium is scanned using a large area source and a point detector (configuration 3).
6. A third image ($I_C$) is generated using the same method as in 2 but using the configuration 3.
7. Image $I_B$ is subtracted from image $I_A$ to enhance structures located close to the output surface of the scattering medium.
8. Image $I_C$ is subtracted from image $I_A$ to enhance structures located close to the input surface of the scattering medium.
9. Image $I_A$ is subtracted from the sum of images $I_B$ and $I_C$ to produce an image wherein the centrally-located structures are enhanced relative to those close to the surface.

Note that other combination of images $I_A$, $I_B$ and $I_C$ or other data processing involving $I_A$, $I_B$ and $I_C$ may also result in obtaining relevant information.

In the summary given above, a point source refers to the injection of light in a medium over a small area; a large area source refers to the injection of light in the medium over a large area; a point detector refers to the detection of light that emerges from the medium over a small area; a large area detector refers to the detection of light that emerges from the medium over a large area. Note again that "small area" refers to a surface whose diameter is small compared to the medium thickness while "large area" refers to a surface whose diameter is on the same order of magnitude as the medium thickness. The appropriate input and output area sizes may be determined empirically for any given turbid medium to be subjected to analysis.

We claim:

1. A method for collecting optical imaging data for generating an image of a turbid medium with an enhancement of image data related to at least one longitudinal zone defined by spatial position between an optical source and an optical detector, the method comprising:

arranging an optical source and an optical detector on opposite sides of a turbid medium;

selecting a plurality of aperture configurations for said source and said detector in accordance with said zone selected, wherein said aperture configurations are selected from at least:

a small aperture source and small aperture detector for enhancing image data related to a longitudinal zone proximal said source and said detector;

a small aperture source and large aperture detector for enhancing image data related to a longitudinal zone proximal said source; and a large aperture source and small aperture detector for enhancing image data related to a longitudinal zone proximal said detector;

scanning said source and said detector over said opposite sides using said plurality of aperture configurations to collect said image data; and combining said image data collected from said plurality of aperture configurations to generate said image of the turbid medium with said enhancement of image data related to said at least one longitudinal zone.

2. The method as claimed in claim 1, wherein said combining comprises at least one of adding and subtracting said image data collected from one of said plurality of aperture configurations and said image data collected from another of said plurality of aperture configurations.

3. The method as claimed in claim 2, wherein said image data collected comprises an image data set $I_A$ corresponding to said small aperture source and small aperture detector configuration, an image data set $I_B$ corresponding to said small aperture source and large aperture detector configuration, said combining comprises essentially $I_A-I_B$ to enhance structures located close to a detector surface side of the turbid medium.

4. The method as claimed in claim 2, wherein said image data collected comprises an image data set $I_A$ corresponding to said small aperture source and small aperture detector configuration, an image data set $I_C$ corresponding to said large aperture source and small aperture detector configuration, said combining comprises essentially $I_A-I_C$ to enhance structures located close to a source surface side of the turbid medium.

5. The method as claimed in claim 1, wherein said plurality of configurations are three in number, wherein said image data collected comprises a first image data set $I_A$ corresponding to said small aperture source and small aperture detector configuration, a second image data set $I_B$ corresponding to said small aperture source and large aperture detector configuration, and a third image data set $I_C$ corresponding to said large aperture source and small aperture detector configuration.

6. The method as claimed in claim 5, wherein said combining comprises essentially $I_B+I_C-I_A$ to enhance structures located centrally relative to structures located close to a source surface side and to a detector surface side of the turbid medium.

7. The method as claimed in claim 5, wherein said combining comprises a combination of essentially $I_B+I_C-I_A$ with essentially $I_A-I_B$ and essentially $I_A-I_C$ to an enhanced image throughout a plurality of longitudinal zones.

8. A method for collecting optical imaging data for generating an image of a turbid medium with an enhancement of image data related to at least one longitudinal zone defined by spatial position between an optical source and an optical detector, the method comprising:

arranging an optical source and an optical detector on opposite sides of a turbid medium;

selecting a plurality of aperture configurations for said source and said detector in accordance with said zone selected, wherein said aperture configurations comprise a large aperture source and small aperture detector for enhancing image data related to a longitudinal zone proximal said detector and at least one of:

a small aperture source and small aperture detector for enhancing image data related to a longitudinal zone proximal said source and said detector; and a small aperture source and large aperture detector for enhancing image data related to a longitudinal zone proximal said source;

scanning said source and said detector over said opposite sides using said plurality of aperture configurations to collect said image data to obtain a plurality of image data sets for said turbid medium, said image data sets possessing different longitudinal zone characteristics enhancement properties.

9. The method as claimed in claim 8, wherein said plurality of configurations are three in number, wherein said image data collected comprises a first image data set $I_A$ corresponding to said small aperture source and small aperture detector configuration, a second image data set $I_B$ corresponding to said small aperture source and large aperture detector configuration, and a third image data set $I_C$ corresponding to said large aperture source and small aperture detector configuration.

* * * * *